(12) United States Patent
Babaev

(10) Patent No.: US 7,740,645 B2
(45) Date of Patent: Jun. 22, 2010

(54) APPARATUS AND METHOD FOR TREATING SOFT TISSUE INJURIES

(75) Inventor: Eilaz Babaev, Minnetonka, MN (US)

(73) Assignee: AB Ortho, LLC, Minnetonka, MN (US)

( * ) Notice: Subject to any disclaimer, the term of this patent is extended or adjusted under 35 U.S.C. 154(b) by 76 days.

(21) Appl. No.: 11/737,114

(22) Filed: Apr. 18, 2007

(65) Prior Publication Data

US 2007/0185527 A1 Aug. 9, 2007

Related U.S. Application Data

(63) Continuation-in-part of application No. 11/737,073, filed on Apr. 18, 2007, and a continuation-in-part of application No. 11/252,680, filed on Oct. 18, 2005.

(51) Int. Cl.
*A61B 17/00* (2006.01)

(52) U.S. Cl. ....................................... 606/204; 601/134

(58) Field of Classification Search ................. 606/185, 606/189, 204; 601/134
See application file for complete search history.

(56) References Cited

U.S. PATENT DOCUMENTS

| | | | |
|---|---|---|---|
| 1,481,354 A | 1/1924 | Dingfeld | |
| 1,554,510 A | * 9/1925 | Kirby | ............................ 15/188 |
| 2,091,276 A | 8/1937 | Gilbert | |
| 3,586,001 A | 6/1971 | Sanderson | |
| 3,970,081 A | 7/1976 | Applegate | |
| 4,081,150 A | 3/1978 | Tuson | |
| 4,162,672 A | 7/1979 | Yazaki | |
| 4,243,028 A | 1/1981 | Puyana | |
| 4,308,861 A | 1/1982 | Kelly | |
| 4,319,574 A | 3/1982 | Sun et al. | |
| 4,378,009 A | 3/1983 | Rowley | |
| 4,479,495 A | 10/1984 | Isaacson | |
| 4,527,566 A | 7/1985 | Abare | |
| 4,590,939 A | 5/1986 | Sakowski | |
| 4,628,918 A | 12/1986 | Johnson | |
| 4,716,898 A | 1/1988 | Chauve et al. | |
| 4,905,998 A | 3/1990 | Last | |
| 4,913,755 A | 4/1990 | Grim | |
| 4,991,234 A | 2/1991 | Greenberg | |
| 4,997,438 A | 3/1991 | Nipper | |
| 5,010,896 A | 4/1991 | Westbrook | |
| 5,027,801 A | 7/1991 | Grim | |
| 5,152,302 A | 10/1992 | Fareed | |

(Continued)

FOREIGN PATENT DOCUMENTS

CH 683822 5/1994

(Continued)

*Primary Examiner*—Todd E Manahan
*Assistant Examiner*—Diane Yabut

(57) ABSTRACT

An apparatus and method is provided for treating injured muscles before, during, and/or after physical activity. Practicing the method of the present involves pressing a plurality of pressure applicators against the skin proximate to a muscle for a sustained period of time. The pressure applicators pressed against the body can be either pins, support members, and/or any combination thereof. The support members may be secured to the therapeutic surface of a therapeutic body as to create an apparatus in accordance with the present invention. In such an apparatus, the base of pressure applicator is secured to the therapeutic surface such that the distal end of the pressure applicator extends away from the therapeutic surface.

6 Claims, 4 Drawing Sheets

U.S. PATENT DOCUMENTS

| | | |
|---|---|---|
| 5,165,402 A | 11/1992 | McCoy |
| 5,190,033 A | 3/1993 | Johnson |
| 5,250,067 A | 10/1993 | Gelfer et al. |
| 5,295,951 A | 3/1994 | Fareed |
| 5,295,996 A | 3/1994 | Fareed |
| 5,312,350 A | 5/1994 | Jacobs |
| 5,338,290 A | 8/1994 | Aboud |
| 5,368,549 A | 11/1994 | McVicker |
| 5,441,058 A | 8/1995 | Fareed |
| 5,445,647 A | 8/1995 | Choy |
| 5,449,379 A | 9/1995 | Hadtke |
| 5,601,598 A | 2/1997 | Fisher |
| 5,607,749 A * | 3/1997 | Strumor ................ 428/156 |
| 5,695,520 A | 12/1997 | Bruckner |
| 5,735,868 A | 4/1998 | Lee |
| 5,774,424 A | 6/1998 | Yoo |
| 5,848,981 A | 12/1998 | Herbanson |
| 5,865,775 A | 2/1999 | Peoples |
| 5,901,379 A | 5/1999 | Hirata |
| 5,957,951 A | 9/1999 | Cazaux et al. |
| 5,971,947 A | 10/1999 | McNally |
| 6,007,508 A | 12/1999 | Reinhardt et al. |
| 6,027,521 A | 2/2000 | Ourada |
| 6,146,347 A | 11/2000 | Porrata |
| 6,149,617 A | 11/2000 | McNally et al. |
| 6,149,618 A | 11/2000 | Sato |
| 6,361,549 B1 * | 3/2002 | Asatourian et al. .......... 606/204 |
| 6,398,749 B1 | 6/2002 | Slautterback |
| 6,463,934 B1 | 10/2002 | Johnson et al. |
| 6,478,760 B2 | 11/2002 | Darcey |
| 2002/0082543 A1 | 6/2002 | Park et al. |
| 2004/0055076 A1 | 3/2004 | Yoo |
| 2006/0047295 A1 * | 3/2006 | Abramov .................... 606/189 |

FOREIGN PATENT DOCUMENTS

| | | |
|---|---|---|
| DE | 29913207 | 12/1999 |
| DE | 102005017587 A1 | 4/2006 |
| WO | 9929236 A1 | 6/1999 |

* cited by examiner

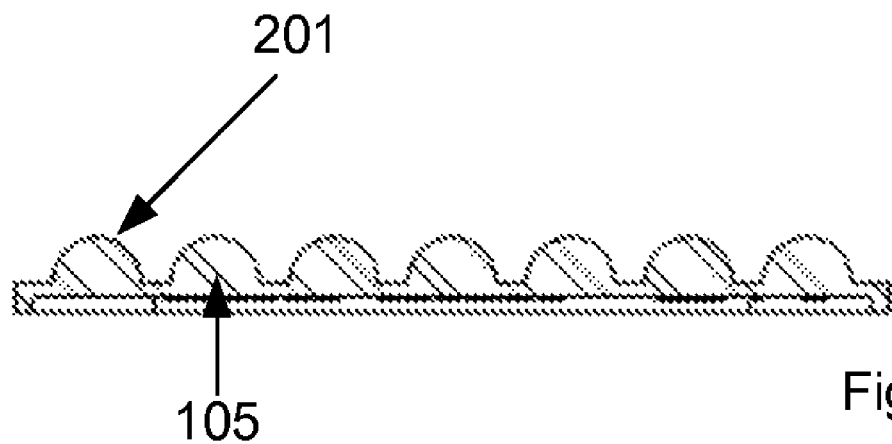
Figure 2a
Figure 2b
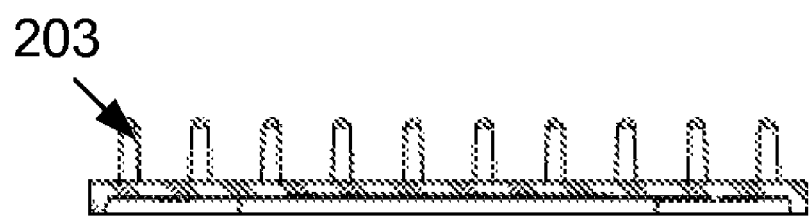
Figure 2c
Figure 2

APPARATUS AND METHOD FOR TREATING SOFT TISSUE INJURIES

CROSS REFERENCE TO RELATED APPLICATIONS

This application is a continuation-in-part of U.S. patent application Ser. No. 11/252,680, filed Oct. 18, 2005, the teachings of which are hereby incorporated by reference, and a continuation-in-part of U.S. patent application Ser. No. 11/737,073, filed Apr. 18, 2007, the teachings of which are hereby incorporated by reference.

BACKGROUND OF THE INVENTION

1. Field of the Invention

The present invention relates to orthopedic devices and treatment methods. More particularly, the present invention relates to orthopedic devices and methods utilizing a plurality of discrete pressure points.

2. Description of the Related Art

Strained, fatigued, or otherwise injured muscles are generally treated by the use of non-steroidal anti-inflammatory drugs (NSAIDs) prior to, after, or during physical activities.

External support devices, such as bandages, slings, or braces, are also often used to treat injured muscles prior to, after, or during physical activities. The aforementioned devices typically elicit a therapeutic benefit on injured muscles by providing support, inhibiting the massive movement of extensor and flexor muscles, absorbing shock, and may enable the warming or cooling of injured muscles.

Chinese acupuncture, well known and recognized worldwide, but not fully appreciated, can also be used for treating injured muscles. During acupuncture therapy, needles are inserted into the body at defined bioactive points. The needles usually remain in the body for a defined period of time. The administration of acupuncture therapy requires a skilled, and in some localities a certified, practitioner.

Acupressure is a derivation of acupuncture therapy. During acupressure therapy, a skilled practitioner applies mechanical pressure to specific bioactive points, while being careful to not apply a harmful amount of pressure.

SUMMARY OF THE INVENTION

The present invention is directed towards an apparatus and method for the providing therapy to injured muscles before, during, and/or after physical activity. Capable of self-administration by the user, the present invention avoids the need of skilled and/or certified practitioners. Not requiring the insertion of needles and/or similar devices into the body, the present invention avoids the risk of infection associated with acupuncture therapy. Providing therapeutic pressure simultaneously along multiple points and/or in different directions, such as, but not limited to, radial, longitudinal, and/or any combination thereof, the present invention may elicit superior a therapeutic effect than conventional tension bandages. In addition to the previously enumerated advantages over the short comings of the existing devices and methods, the present invention may also provide additional advantages and improvements that will be recognizes by people of ordinary skill in the art upon review of the present disclosure.

The method of the present invention comprises the steps of pressing a plurality of pressure applicators against the skin proximate to and/or over a muscle for a sustained period of time. The pressure applicators pressed against the skin can be either pins, support members, and/or any combination thereof. An apparatus in accordance with the present invention comprises a therapeutic body, a therapeutic surface on one side of the therapeutic body, and plurality of pressure applicators. The pressure applicators comprise a base secured to the therapeutic surface and a distal end extending away from the therapeutic surface. The pressure applicators may apply a generally directed pressure radially and longitudinally to the muscle being treated. The pressure applicators may also absorb shock.

When the plurality of pressure applicators comprises in whole or in part a plurality of pins, the density of the pins on the therapeutic surface should be between density between 3 pins/cm$^2$ and 1,000 pins/cm$^2$. Each pin is defined as an ordinary pin or similar protrusion providing pressure at a localized region. A plurality of pins with a density between 3 pins/cm$^2$ and 1,000 pins/cm$^2$ may concentrate pressure at multiple locations over the muscle being treated. The use of a plurality pins will typically distribute the force applied to the skin surface by each pin, thereby preventing the insertion, or penetration, of the pins into the body. The use of multiple pins may also stimulate dendrites beneath the area of the skin to which the pins are pressed. Contacting the skin at various orientations with the respect to skin surface, and the use of multiple pins may stretch the skin surface as to open pores within the skin.

The pins utilized with the present invention may have a pointed, conical, spherical, or curvilinear distal end. Different configurations of the distal ends of the pins may be useful for different therapeutic purposes. For instance, pins with pointed distal ends may be utilized to relieve acute muscle. Spherical or rounded distal ends may be utilized relieve prolonged pain and/or muscle tension.

When the plurality of pressure applicators comprises in whole or in part support members, the support members chosen should have an arced cross section on at least one axis transecting the support member, with the apex of the arc extending away from the therapeutic surface. Before, during, and/or after physical activity, the support members are placed in contact with the body proximate to and/or over an injured muscle, with the therapeutic surface facing the skin. Pressure is then applied to the support members as a whole. The applied pressure is distributed amongst the support members contacting the body. Translating the pressure applied to the support member into a compressive stress, the arched cross-sections of the support members provides a supportive pressure to a muscle.

When the present invention is pressed to the skin, the support members may elicit a therapeutic effect on a muscle proximate to and/or over which the present invention is located. Providing supportive pressure, the support members may bring about pain relief in a manner similar to that of acupressure therapy. Supporting the muscle, the support members may absorb shock. Distributing the supportive pressure across the support members may cause the skin over the muscle to stretch as to open pores in the skin surface. The opening of pores in the skin surface may increase absorption of oxygen through the skin. Distributing supportive pressure across the support members may cause stretching of the muscle beneath and/or proximate to the support members. Other therapeutic benefits and/or mechanisms of actions, in addition to those listed, may be elicited by the support members of the present invention.

BRIEF DESCRIPTION OF DRAWINGS

FIG. 2 depicts cross sectional views of four embodiments of the apparatus of the present invention.

DETAILED DESCRIPTION

Figure 1:
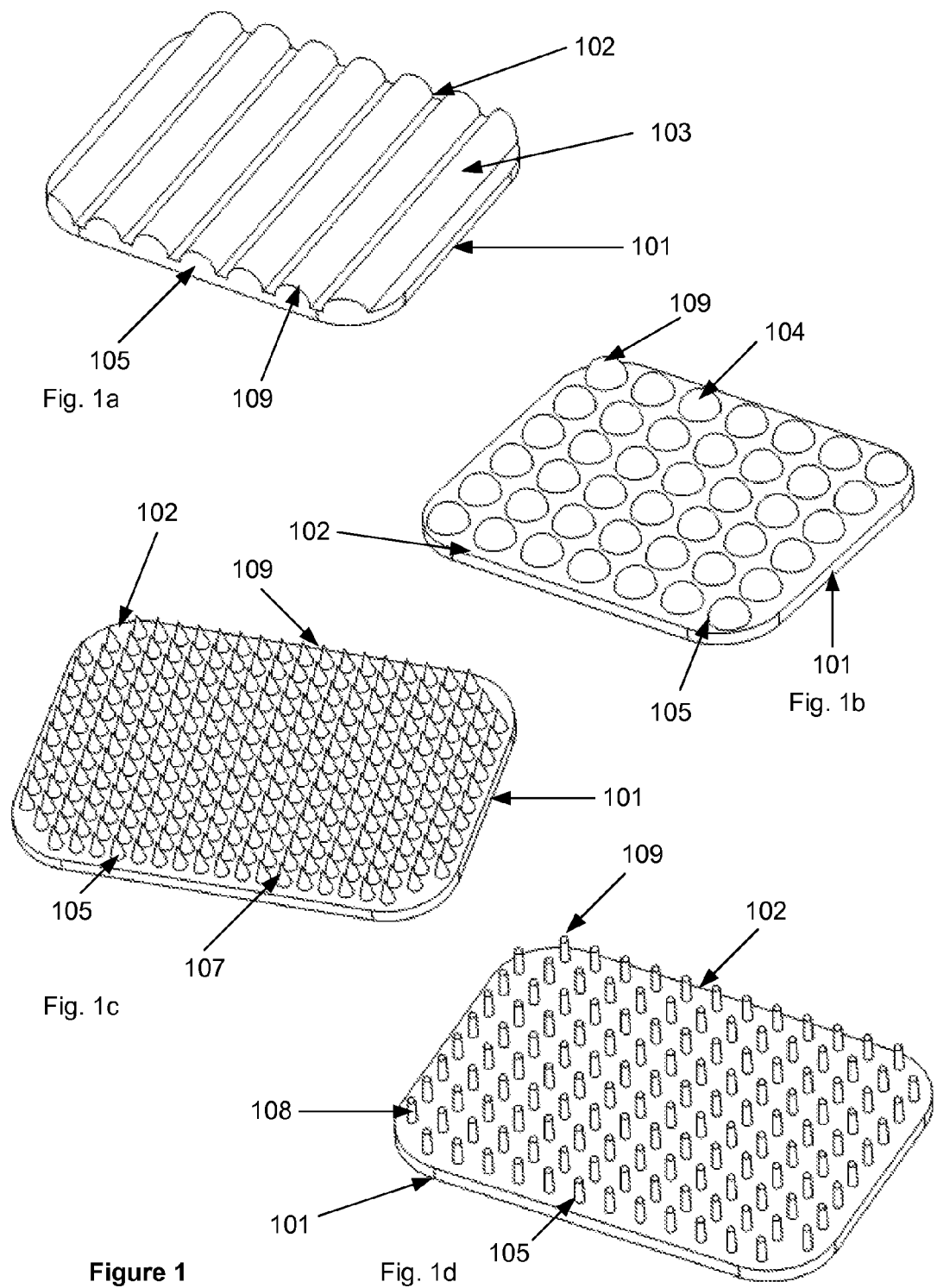
FIG. 1 depicts three-dimensional views of four embodiments of the apparatus of the present invention.

FIG. 1 depicts three-dimensional views (FIG. 1a FIG. 1b, FIG. 1c, and FIG. 1d) of four embodiments of the apparatus of the present invention. FIG. 2 depicts three cross-sectional views (FIG. 2a, FIG. 2b, and FIG. 2c) of the depicted embodiments of FIG. 1. FIG. 2a is a cross-sectional view common to both of the embodiments depicted in FIG. 1a and FIG. 1b. The present invention comprises a therapeutic body 101, a therapeutic surface 102 on side of the therapeutic body 101, and a plurality of pressure applicators (e.g. 103, 104, 107, and 108). Each of the example pressure applicators 103, 104, 107, and 108 comprises a base 105 secured to the therapeutic surface, and a distal end 109 extending away from therapeutic surface 102.

The pressure applicators may be support members 103 and 104, as depicted in FIGS. 1a, 1b, and 2a. Support members, such as those depicted in FIG. 1a, 1b, and 2a, comprise an arc 201 spanning the base 105 along at least one axis. As depicted in FIG. 1a, arc 201 may be extruded along a second axis forming vaults 103. The arc 201 may also be revolved along one axis forming domes 104, as depicted in FIG. 1b. Other support member configurations are possible and in accordance with the present invention, so long as there is an arc spanning at least one axis of the base.

The pressure applicators may be pointed pins 107, as depicted in FIGS. 1c and 2b, and/or rounded pins 108, as depicted in FIGS. 1d and 2c. When the pressure applicators are pins, the density of the pins on the therapeutic surface should be between density between 3 pins/cm$^2$ and 1,000 pins/cm$^2$. In preferred embodiments, the pin density is between 10 pins/cm$^2$ and 200 pins/cm$^2$. A density of 100 pins/cm$^2$ is suggested. Pins utilized as pressure applicators may have a pointed distal end 202 (FIGS. 1c and 2b) or a rounded distal end 203 (FIGS. 1d and 2c).

The pressure applicators may be made from plastic and/or a polymer. The pressure applicators may also be made from a variety of materials. Precious metals such as, but not limited to, gold, silver, and/or platinum, may be used in constructing the support members.

Therapeutic body 101 may be made from a compliant material or rigid material. If a rigid material is used, it may be desirable to segment therapeutic body 101 as to enable therapeutic body 101 to conform to the wearer's body.

Figure 3:
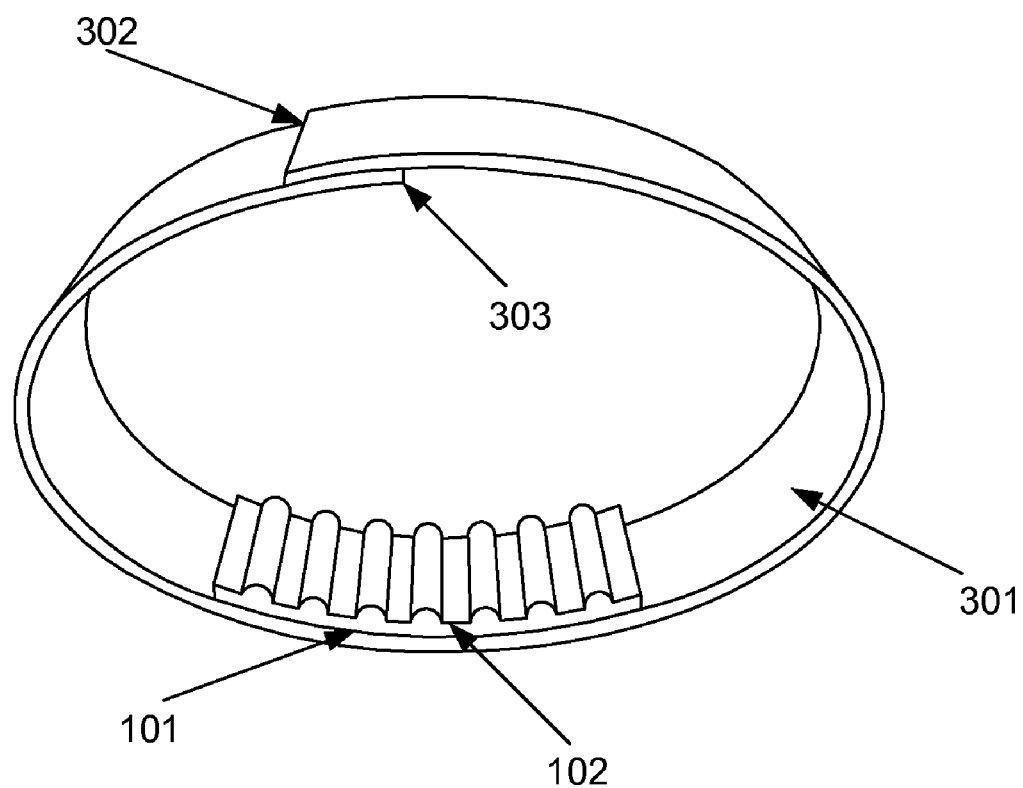
FIG. 3 depicts a three-dimensional view an embodiment of the apparatus of the present invention secured to a strap.

Before, during, and/or after physical activity, such as, but not limited to, exercise, playing sports, and/or manual labor, the apparatus of the present invention is pressed against the body, with therapeutic surface 102 facing the body. Preferably, the apparatus of the present invention is pressed proximate to and/or over an injured muscle. The apparatus of the present invention may be pressed against the body and/or secured in place with the use of a strap 301, depicted in FIG. 3. Strap 301 may be fastened around a portion of the body such as, but not limited to, a limb, a shoulder, the trunk, and/or the head by tying ends 302 and 303 together. Alternatively, Velcro attached to end 302 may be used to secure strap 301 to a portion of the body. Strap 301 may also be secured by the use of snaps, a buckle, buttons, and/or numerous other methods readily recognizable to a person of ordinary skill in the art. The apparatus of the present invention may also be secured in place and/or pressed against the body with the use of a sling, brace, bandage, tape, and/or numerous other devices readily recognizable to a person of ordinary skill in the art.

Regardless of the device used to secure and/or press the apparatus of the present invention against a portion of the body, it is preferable the apparatus of the present invention be secured to the device. Ideally, therapeutic body 101 is removably secured to strap 301 or a similar device. Therapeutic body 101 may be removably secured to strap 301 or a similar device by including an eye or plurality of eyes on therapeutic 101 through which strap 301 or a similar device is threaded. Therapeutic body 101 may also be removably secured to strap 301 or a similar device by attaching a piece of Velcro on therapeutic body 101 opposite therapeutic surface 102 and a mating piece of Velcro on strap 301 or a similar device. As an alternative to Velcro, temporary adhesives, snaps, and/or numerous other methods readily recognizable to person or ordinary skill in the art may be used to removably secure therapeutic body 101 to strap 301 or similar devices.

Vaulted support members 103 may be desirable when the user is experiencing pain localized to a particular muscle or group of muscles during physical activity. In such a situation, vaulted support members 103 should be pressed against the body proximate to and/or over the injured muscles until the pain subsists and/or physical activity is terminated. If a therapeutic body 101 with a therapeutic surface 102 measuring 5 cm by 6 cm is used, seven vaults with a length of 5 cm, a width of 6 mm, and a height of 3 mm may be positioned uniformly over therapeutic surface 102, as depicted in FIG. 1a. Other vault dimensions and density are equally possible. Furthermore, therapeutic surface 102 may be larger or smaller than the size previously enumerated. When vaulted support members are used, the apparatus present invention should, but need not, be oriented such that vaulted support members 103 run with the thread of the muscle or muscles.

Domed support members 104 may be desirable when the user is experiencing a shooting during physically activity. In such a situation, domed support members 104 should be pressed against the body proximate to and/or over the injured muscles from which the shooting pain originates until the pain subsists and/or physical activity is terminated. If a therapeutic body 101 with a therapeutic surface 102 measuring 5 cm by 6 cm is used, 42 domes with a base diameter of 6 mm and a height of 3 mm may be positioned uniformly over therapeutic surface 102, as depicted in FIG. 1b. Other dome dimensions and density are equally possible. Furthermore, therapeutic surface 102 may be larger or smaller than the size previously enumerated.

Pointed pins 107 may be desirable when the user is experiencing an acute pain following and/or prior to physical activity. In such as situation, pointed pins 107 should be pressed against the body proximate to and/or over the injured muscle until the pain subsists and/or for a period of approximately 15 minutes or less. Longer periods of treatment with pointed pins 107 may also be utilized.

Rounded pins 108 may be desirable when the user is experience a prolonged pain and/or muscle tension following and/or prior to physical activity. One example of a prolonged pain may be a dull lingering pain in the muscle. Other types of prolonged pain may also be treated with rounded pins 108. In such as situation, rounded pins 108 should be pressed against the body proximate to and/or over the injured muscled until the pain and/or tension subsists and/or for a period of approximately 60 minutes of less. Longer periods of treatment with rounded pin 108 may also be utilized.

It should be appreciated that vaulted support members 103, domed support members 104, pointed pins 107, and rounded pins 108 may be utilized in combination or isolation.

Regardless of the configuration, size, or density chosen, the pressure applicators may be secured to the therapeutic surface 102 in a variety patterns. Possible patterns of the pressure applicators on the therapeutic surface 102 include, but are not limited to, linear, sinusoidal, triangular, rectangular, circular, spiral, and/or any combination thereof. In some situations, it may be preferable to select a support member pattern that approximates and/or resembles the configuration, shape, and/or thread of the injured muscle. Therapeutic body 101 and/or therapeutic surface 102 may be configured to match the support pattern utilized.

Figure 4:
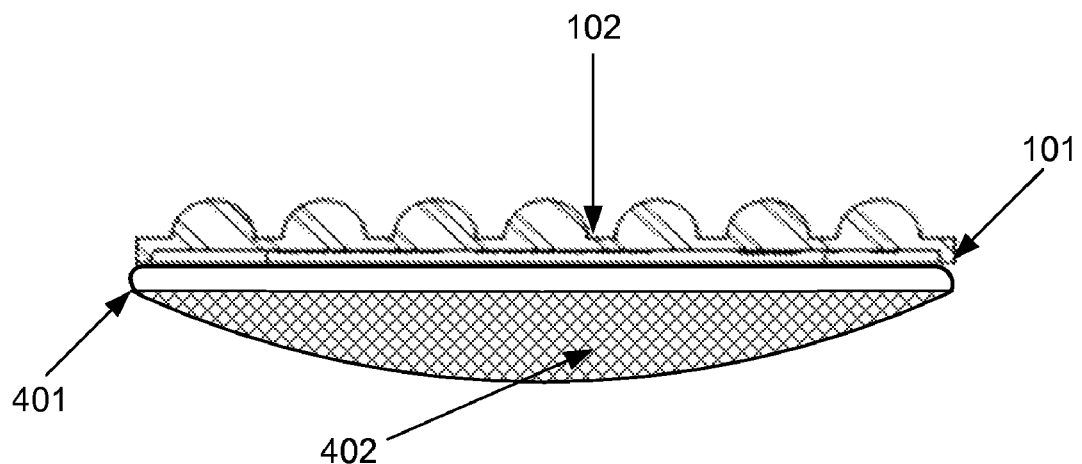
FIG. 4 depicts a cross-sectional view of an embodiment of the apparatus of the present invention secured to a bladder.

As depicted in FIG. 4, a bladder 401 may be secured to therapeutic body 101 opposite therapeutic surface 102. The bladder may be filled with a substance 402 hotter or colder than the body such as, but not limited, gas, solid, fluid and/or gel. Substance 402 within the bladder may contain chemicals that react exothermically or endothermically. Such chemicals are readily recognizable to a people of ordinary skill in the art. When bladder 401 is filled with a substance 402 hotter than the body and/or chemicals reacting exothermically, heat from bladder 401 will be transferred to muscles in contact with and/or proximate to the apparatus of the present invention. Conversely, when bladder 401 is filled with a substance 402 colder than the body and/or chemicals reacting endothermically, heat will be transferred from muscles in contact with and/or proximate to the present invention to bladder 401. Transferring heat from bladder 401 to injured muscles may elicit several therapeutic benefits such as, but not limited to, increasing blood flow to the muscles, and/or relaxing the muscles. Transferring heat from injured muscles to bladder 401 may elicit several therapeutic benefits such as, but not limited to, decreasing swelling, decreasing inflammation, and/or dulling pain.

Arc as used herein refers to a segment of a differentiable curve.

It should be appreciated that elements described with singular articles such as "a", "an", and "the" or otherwise described singularly may be used in plurality. It should also be appreciated that elements described in plurality may be used singularly.

Although specific embodiments of apparatuses and methods have been illustrated and described herein, it will be appreciated by people of ordinary skill in the art any arrangement, combination, and/or sequence that is calculated to achieve the same purpose may be substituted for the specific embodiments shown. It is to be understood that above description is intended to be illustrative and not restrictive. Combinations of the above embodiments and other embodiments as wells as combinations and sequences of the above methods and other methods of use will be apparent to individuals possessing skill in the art upon review of the present disclosure. The scope of the present invention should be determined with reference to the appended claims, along with the full scope of equivalents to which such claims are entitled.

I claim:

1. A method of providing therapy to muscles comprising the steps of:
   a. pressing a plurality of pressure applicators against the skin proximate to an injured muscle for sustained periods of time;
   b. wherein pressure applicators consisting of support members having an arced cross section on at least one axis transecting the support member are pressed against the skin proximate to an injured muscle during physical activity and pressure applicators consisting of pins having a pointed distal end and arranged on a therapeutic surface in a density between 3 pins/cm$^2$ and 1,000 pins/cm$^2$ are pressed against the skin proximate to an injured muscle subsequent to said physical activity.

2. The method of claim 1, further comprising the step of securing the pressure applicators against the skin with a device selected from the group consisting of a strap, sling, brace, bandage, and tape.

3. The method of claim 1, wherein the pins are pressed against the skin for a period of approximately 15 minutes or less.

4. The method of claim 1, wherein the pins are pressed against the skin proximate to a muscle experiencing acute pain.

5. The method of claim 1, wherein the arc of the support member is extruded along an axis and the support member is pressed against the skin proximate to a muscle experiencing pain.

6. The method of claim 1, wherein the arc of the support member is revolved along one axis and the support member is pressed against the skin proximate to a muscle from which a shooting pain originates.

* * * * *